(12) United States Patent
Shimko

(10) Patent No.: US 8,486,120 B2
(45) Date of Patent: Jul. 16, 2013

(54) IMPLANT WITH DEPLOYABLE STABILIZERS

(75) Inventor: Daniel Andrew Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 398 days.

(21) Appl. No.: 12/777,492

(22) Filed: May 11, 2010

(65) Prior Publication Data

US 2011/0282396 A1 Nov. 17, 2011

(51) Int. Cl.
*A61B 17/04* (2006.01)
*A61B 17/86* (2006.01)
*A61F 2/08* (2006.01)
*F16B 13/06* (2006.01)

(52) U.S. Cl.
USPC .............................. 606/303; 411/55

(58) Field of Classification Search
USPC ............... 606/310, 303; 411/21, 22, 55
See application file for complete search history.

(56) References Cited

U.S. PATENT DOCUMENTS

| | | | | |
|---|---|---|---|---|
| 3,269,251 A | * | 8/1966 | Bass | 411/21 |
| 3,953,140 A | * | 4/1976 | Carlstrom | 403/258 |
| 4,011,602 A | | 3/1977 | Rybicki et al. | |
| 4,220,712 A | | 9/1980 | Staffolani | |
| 4,468,201 A | | 8/1984 | Fukuyo | |
| 4,531,916 A | | 7/1985 | Scantelbury et al. | |
| 4,636,121 A | * | 1/1987 | Miller | 411/21 |
| 5,004,421 A | | 4/1991 | Lazarof | |
| 5,417,569 A | | 5/1995 | Perisse | |
| 5,470,230 A | | 11/1995 | Daftary et al. | |
| 5,489,210 A | * | 2/1996 | Hanosh | 433/173 |
| 5,665,122 A | | 9/1997 | Kambin | |
| 5,704,752 A | * | 1/1998 | Logerot | 411/503 |
| 5,759,033 A | | 6/1998 | Elia | |
| 5,849,004 A | * | 12/1998 | Bramlet | 606/232 |
| 5,863,200 A | | 1/1999 | Hamada et al. | |

(Continued)

FOREIGN PATENT DOCUMENTS

| | | |
|---|---|---|
| KR | 20020072632 A | 9/2002 |
| KR | 20040078170 A | 9/2004 |
| WO | 2009137545 A1 | 11/2009 |

OTHER PUBLICATIONS

Keystone Dental, Inc., Prima Implant System, Surgical Manual, RevA, Jun. 2008, pp. 1-56, Burlington, MA.

(Continued)

*Primary Examiner* — Kevin T Truong
*Assistant Examiner* — David Bates
(74) *Attorney, Agent, or Firm* — Sorell Lenna & Schmidt LLP

(57) ABSTRACT

An implant includes a body having an upper and lower ends, a longitudinal bore defined by a threaded interior surface, and a threaded exterior surface; at least one stabilizer arm associated with a corresponding longitudinal slot in the body, the stabilizer arm being hingedly attached to the body and having a bone gripping protuberance projecting laterally outward therefrom. The stabilizer arm is movable from a first position wherein the bone gripping protuberance is positioned within the bore and a second fully extended position wherein the bone gripping protuberance is positioned outside the threaded exterior surface of the body. The stabilizer arm is resiliently biased to the first position. A camming member is movable through the bore of the body from an initial position to a final position wherein the stabilizer arm is moved to the second stabilizer arm position.

10 Claims, 5 Drawing Sheets

U.S. PATENT DOCUMENTS

| | | | | |
|---|---|---|---|---|
| 5,888,067 | A | 3/1999 | Gibbs et al. | |
| 5,931,674 | A | 8/1999 | Hanosh et al. | |
| 5,951,288 | A | 9/1999 | Sawa | |
| 6,126,663 | A * | 10/2000 | Hair | 606/324 |
| 6,126,689 | A | 10/2000 | Brett | |
| 6,146,406 | A | 11/2000 | Shluzas et al. | |
| 6,213,774 | B1 | 4/2001 | Lazarof | |
| 6,214,050 | B1 | 4/2001 | Huene | |
| 6,227,860 | B1 | 5/2001 | Hobo | |
| 6,287,343 | B1 | 9/2001 | Kuslich et al. | |
| 6,447,546 | B1 * | 9/2002 | Bramlet et al. | 623/17.16 |
| 6,520,991 | B2 | 2/2003 | Huene | |
| 6,688,822 | B2 * | 2/2004 | Ritter et al. | 411/21 |
| 6,758,672 | B2 | 7/2004 | Porter et al. | |
| 6,863,530 | B2 | 3/2005 | McDevitt | |
| 6,955,691 | B2 * | 10/2005 | Chae et al. | 623/17.16 |
| 6,991,461 | B2 | 1/2006 | Gittleman | |
| 7,179,088 | B2 | 2/2007 | Schulter et al. | |
| 7,377,781 | B1 | 5/2008 | Karapetyan | |
| 7,828,802 | B2 * | 11/2010 | Levy et al. | 606/63 |
| 7,879,036 | B2 * | 2/2011 | Biedermann et al. | 606/62 |
| 8,142,479 | B2 * | 3/2012 | Hess | 606/248 |
| 2002/0160335 | A1 | 10/2002 | Ashman et al. | |
| 2009/0192553 | A1 * | 7/2009 | Maguire et al. | 606/305 |
| 2009/0208905 | A1 | 8/2009 | Vachtenberg | |
| 2010/0055643 | A1 | 3/2010 | Hung | |

OTHER PUBLICATIONS

International Search Report and Written Opinion for PCT/US2011/036120 the counterpart application mailed on Jan. 12, 2012.

* cited by examiner

IMPLANT WITH DEPLOYABLE STABILIZERS

TECHNICAL FIELD

The present invention relates to implants which are surgically placed in bone to provide an anchoring means for a prosthesis or other device. In particular, the implant of the present invention is especially advantageous for use in dental surgery.

BACKGROUND

Implants are widely used in dental surgery for restoration of the jaw anatomy. Implants can be used, for example, for anchoring a dental prosthesis such as an artificial tooth to the jawbone of a patient. Various types of dental implants are disclosed, for example, in U.S. Pat. Nos. 7,179,088, 6,991,461, 6,863,530, 6,227,860, 5,951,288, 5,931,674, 5,863,200, 5,470,230, 5,417,569, and 4,531,916, all of the above references being incorporated by reference herein.

A typical dental implant has a generally cylindrical shaped body which is mounted into a hole pre-drilled in the jawbone. The implant can be threadedly fitted or press fitted into the hole. The prosthesis can then be fixedly mounted to the implant secured within the bone. However, it is possible for the implant to loosen if, for example, the hole is or becomes too big or is improperly drilled. This can result in loss of the implant or prosthesis and require a subsequent operation to remedy the situation. The present disclosure describes a dental implant which can be deploy radially outwardly moving stabilizers within the pre-drilled hole in the jawbone to secure the dental implant with a tight friction fit to the bone structure.

SUMMARY OF THE INVENTION

Accordingly, an implant and method are provided herein for anchoring a prosthesis, such as an artificial tooth to the jawbone. In one embodiment the implant comprises:

(a) a body having an upper end, a lower end, a longitudinal bore defined by a threaded interior surface, and a threaded exterior surface; (b) at least one stabilizer arm associated with a corresponding longitudinal slot in the body, said stabilizer arm being hingedly attached to the body and having a bone gripping protuberance projecting laterally outward therefrom, said stabilizer arm being movable from a first position wherein said bone gripping protuberance is positioned within said bore and a second fully extended position wherein said bone gripping protuberance is positioned outside the threaded exterior surface of the body, said stabilizer arm being resiliently biased to the first position; (c) a camming member longitudinally movable through the bore of said body from an initial position to a final position wherein the stabilizer arm is moved by contact with the camming member to the second stabilizer arm position.

In another embodiment of the implant the at least one stabilizer arm comprises more than one stabilizer arm.

In another embodiment of the implant the at least one stabilizer arm is integrally constructed with the body.

In another embodiment of the implant the stabilizer arm comprises an elongated longitudinally extending member with the bone gripping protuberance projecting from a lower end portion of the stabilizer arm.

In another embodiment of the implant the camming member includes a threaded exterior surface adapted to engage the threaded interior surface of the implant body, and means for mounting a prosthesis including an axial recess defined by a threaded interior surface or an upwardly projecting mounting member.

In another embodiment of the implant the stabilizer arm includes a radially inward extending detent at the lower end portion thereof and the camming member includes a circumferential notch engageable with the detent when the camming member is moved to its final position to lock the camming member in the final position and the stabilizer arm in the fully extended second position.

In another embodiment of the implant the body is fabricated from a polymeric material or a metal.

In another embodiment of the implant the camming member comprises an upper rim having a diameter greater than the diameter of the bore of the body.

Also provided herein is an implant system comprising an implant and an applicator, wherein:

(a) the implant includes: (i) a body having a longitudinal bore defined by a threaded interior surface, a threaded exterior surface, (ii) at least one stabilizer arm associated with a corresponding longitudinal slot in the body, said stabilizer arm being hingedly attached to the body and having a bone gripping protuberance projecting radially outward therefrom, said stabilizer arm being movable from a first position wherein said bone gripping protuberance is positioned within said bore and a second fully extended position wherein said bone gripping protuberance is positioned outside the threaded exterior surface of the body, said stabilizer arm being resiliently biased to the first position, (iii) a camming member longitudinally movable through the bore of said body from an initial position to a final position wherein the stabilizer arm is moved by contact with the camming member to the second stabilizer arm position, and (iv) a reinforcement member; and (b) the applicator includes (i) a threaded drive shaft engageable with the camming member, and (ii) a support frame rotatably engageable with the drive shaft.

In another embodiment of the implant system the body is cylindrical.

In another embodiment of the implant system the body has an upper end and a lower end.

In another embodiment of the implant system the at least one stabilizer arm comprises more than one stabilizer arm.

In another embodiment of the implant system the at least one stabilizer arm is integrally constructed with the body.

In another embodiment of the implant system the stabilizer arm comprises an elongated longitudinally extending member with the bone gripping protuberance projecting from a lower end portion of the stabilizer arm.

In another embodiment of the implant system the camming member includes a threaded exterior surface adapted to engage the threaded interior surface of the implant body, and an axial recess defined by a threaded interior surface.

In another embodiment of the implant system the stabilizer arm includes a radially inward extending detent at the lower end portion thereof and the camming member includes a circumferential notch engageable with the detent when the camming member is moved to its final position to lock the camming member in the final position and the stabilizer arm in the fully extended second position.

In another embodiment of the implant system the drive shaft includes a threaded rod engageable with a corresponding axial threaded bore in the camming member.

In another embodiment of the implant system the cylindrical cap includes a threaded circumferential surface which is engageable with the interior threaded surface of the body and an axial bore through which an upper portion of the drive shaft can be disposed.

Also provided herein is a method for implanting a prosthesis comprising: (a) drilling a hole into a bone; (b) providing an implant which includes: (i) a body having a longitudinal bore defined by a threaded interior surface, a threaded exterior surface, (ii) at least one stabilizer arm associated with a corresponding longitudinal slot in the body, said stabilizer arm being hingedly attached to the body and having a bone gripping protuberance projecting radially outward therefrom, said stabilizer arm being movable from a first position wherein said bone gripping protuberance is positioned within said bore and a second fully extended position wherein said bone gripping protuberance is positioned outside the threaded exterior surface of the body, said stabilizer arm being resiliently biased to the first position, (iii) a camming member longitudinally movable through the bore of said body from an initial position to a final position wherein the stabilizer arm is moved by contact with the camming member to the second stabilizer arm position; (c) inserting the implant into the hole in the bone; and (d) moving the camming member from its initial position to its final position to secure the implant in the bone.

Also provided herein is an implant kit comprising an implant and an applicator, wherein the kit includes (i) an implant body having a longitudinal bore defined by a threaded interior surface, a threaded exterior surface, at least one stabilizer arm associated with a corresponding longitudinal slot in the body, said stabilizer arm being hingedly attached to the body and having a bone gripping protuberance projecting radially outward therefrom, said stabilizer arm being movable from a first position wherein said bone gripping protuberance is positioned within said bore and a second fully extended position wherein said bone gripping protuberance is positioned outside the threaded exterior surface of the body, said stabilizer arm being resiliently biased to the first position, (ii) a camming member configure to be longitudinally movable through the bore of said implant body from an initial position to a final position wherein the stabilizer arm is moved by contact with the camming member to the second stabilizer arm position, and optionally one or more of (iii) a reinforcement member, (iv) a threaded drive shaft engageable with the camming member, and (v) a support frame rotatably engageable with the drive shaft. Also provided herein is an implant kit comprising the elements of an implant as described herein.

BRIEF DESCRIPTION OF THE DRAWINGS

Various embodiments of the invention are described below with reference to the drawings, wherein.

DETAILED DESCRIPTION

Figure 1:
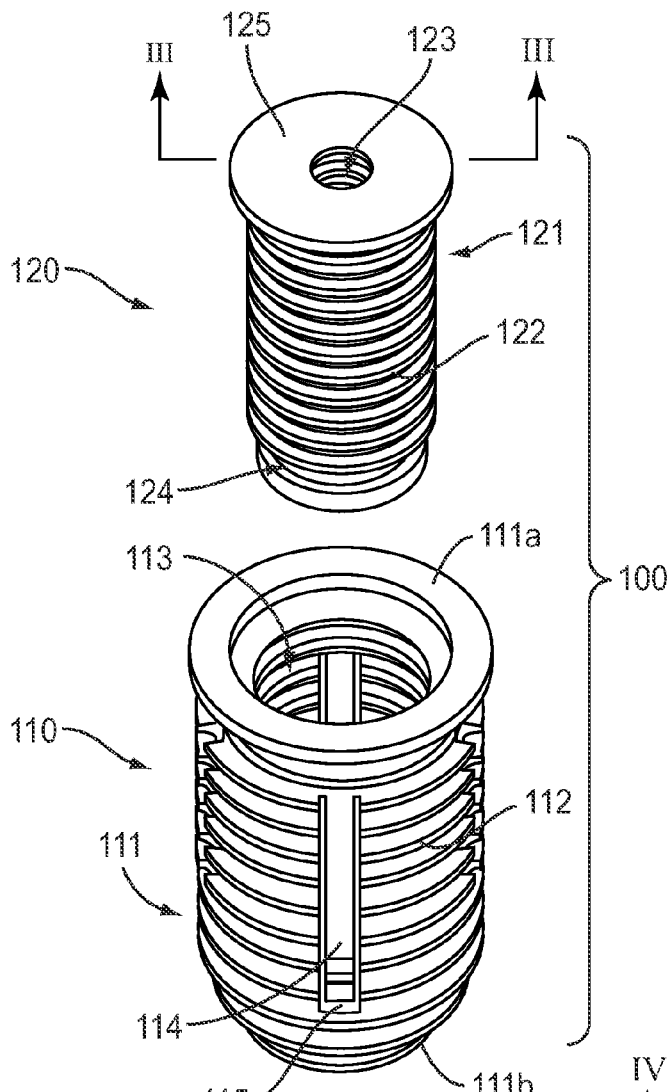
FIG. 1 is an exploded perspective view of an embodiment of the invention.
Figure 2:
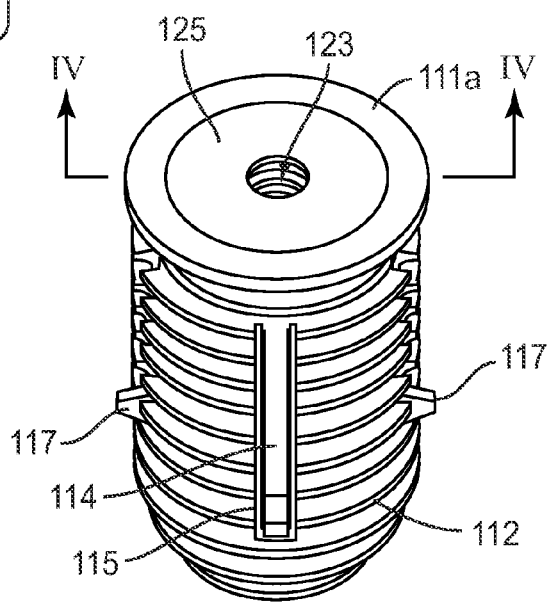
FIG. 2 is a perspective view of the embodiment of FIG. 1.

The present invention may be understood more readily by reference to the following detailed description of the invention taken in connection with the accompanying drawing figures, which form a part of this disclosure and in which like numbers indicate like features. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value.

When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". As used herein, "comprising", containing", "characterized by" and grammatical equivalents thereof are inclusive or open-ended terms that do not exclude additional, unrecited elements or method steps, but will also be understood to include the more restrictive terms "consisting of" and "consisting essentially of."

The following discussion includes a description of an implant system, related components and exemplary methods of employing the implant system in accordance with the principles of the present disclosure. More particularly, the exemplary embodiments of the implant are particularly suitable for use in dental surgery and provide a stable anchoring for a dental prosthesis such as an artificial tooth. Additional embodiments are also disclosed. It should be noted that the implant of the invention can also be used in any type of surgery in which a device is to be attached to bone. Accordingly, the scope of the present invention is not limited to only dental implants. Reference will now be made in detail to the exemplary embodiments of the present disclosure, which are illustrated in the accompanying figures.

Referring now to FIGS. 1 to 4, in one embodiment the implant of the invention 100 includes a shell 110 and an abutment member, i.e., camming core 120. The shell 110 a generally cylindrical body 111 with an upper end 111a and a lower end 111b. Shell body 111 further includes a threaded outer surface 112 and an inner threaded surface defining a threaded bore 113. Shell body 111 further includes at least one, and preferably two or more, stabilizer arms 114, each associated with a corresponding slot 115. Each stabilize arm 114 is flexibly attached to the shell body 111 at an upper bend point 114a and includes a depending elongated shaft 114b at the lower end of which is radially outward projecting bone gripping protuberance 117 and a radially inward projecting locking detent 116.

Figure 3:
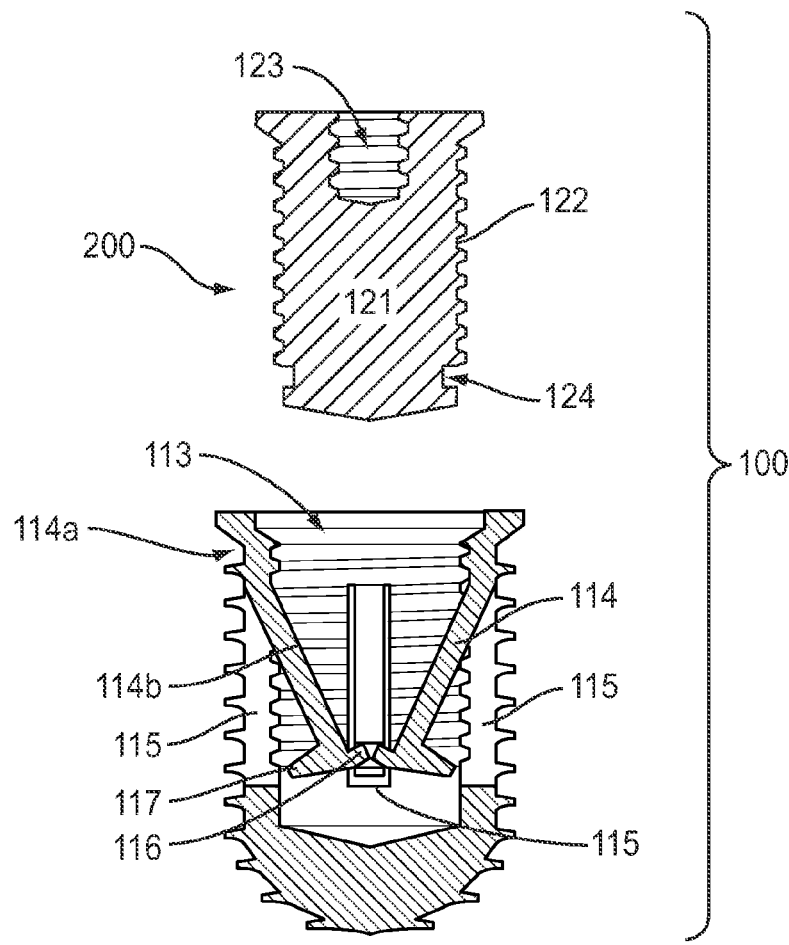
FIG. 3 is an exploded sectional view of the embodiment of FIG. 1.
Figure 4:
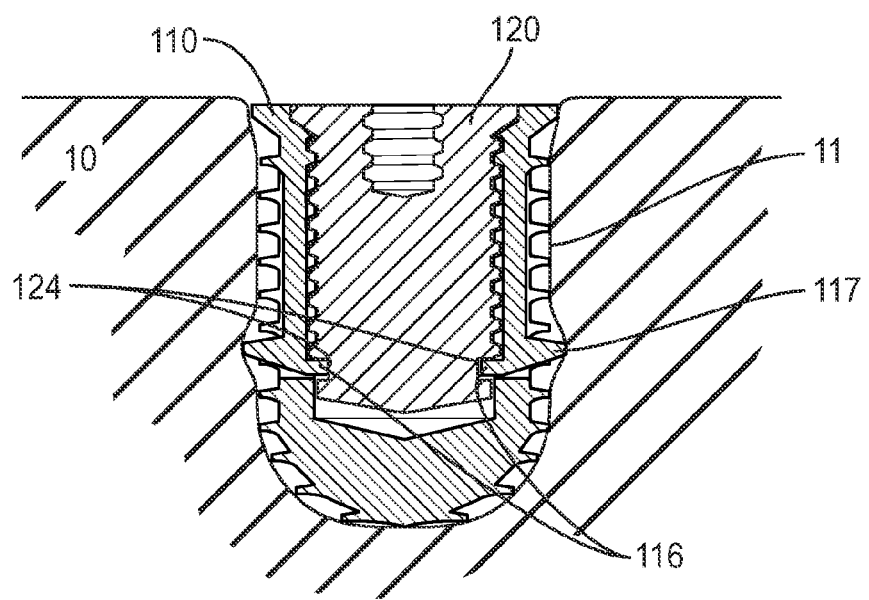
FIG. 4 is a sectional view of the embodiment of FIG. 1 implanted in bone.

The stabilizer arms 114 can be integrally fabricated with shell body 111 as a single piece construction. Stabilizer arms 114 are resiliently based to a radially inward first position as shown in FIG. 3, but are resiliently movable to a second fully extended position as shown in FIG. 4. In the first position of the stabilizer arm, the bone gripping protuberance 117 is located within the bone 113. In the second fully extended position of the stabilizer arm 114, the bone gripping protuberance 117 is positioned beyond the outer surface 112 of the shell body 111 so as to grip the bone into which the implant 100 is secured. The stabilizer arm 114 is configured and dimensioned so as to be disposed through the corresponding slot 115.

The components of the implant system may be fabricated from materials suitable for medical applications, including metals, synthetic polymers, ceramics, bone, bio-compatible materials and/or their composites, depending on the particular application and/or preference of a medical practitioner. For example, components of the implant system, such as, for example, an implant body, an outer surface of the implant body and/or portions thereof, cavities of the implant body, which may be monolithically formed, integrally connected or configured as an insert with the body, fastening elements and/or instruments and/or expanding devices, discussed below, can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO$_4$ composites, ceramics and composites thereof such as calcium phosphate (e.g. SKELITE™ manufactured by Biologix Inc.), rigid polymers including polyphenylene, polyamide, polyimide, polyetherimide, polyethylene, polyurethanes of any durometer, epoxy and/or silicone. Different components of the implant system may have alternative material composites to achieve various desired characteristics such as strength, rigidity, elasticity, compliance, biomechanical performance, durability and radiolucency or imaging preference. The components of the implant system may also be fabricated from a heterogeneous material such as a combination of two or more of the above-described materials.

The implant 100 includes a camming core 120 which is configured and dimensional so as to be received into bore 113 of the shell body 111. More particularly, camming core 120 includes a core body 121 having a circumferential threaded surface 122 adapted to engage the threaded inner surface of the shell body 111 defining the bore 113. A top surface 125 has a diameter larger than the diameter of bore 113 so as to prevent further insertion of the core body 121 into bore 113 and to be flush with upper end 111a of the shell body 111 when the core body 121 has been fully inserted therein. Core body 121 includes means for mounting a prosthesis. Such means can include an axial threaded recess 123 into which a prosthesis can be engaged. In another embodiment such as described below the core body 121 can include an axial threaded upward projection onto which a prosthesis can be screw mounted. Mounting of a prosthesis typically includes the use of a permanent cement for long term adhesive attachment. Core body 121 may further include a circumferential recess 124 in the vicinity of the bottom end thereof. Recess 124 is adapted to receive the locking detent 116 of the stabilizer arms 114 when the core body 121 has been fully inserted into bore 113 of the shell body 111.

Referring especially now to FIGS. 3 and 4, as the core body 121 is screwed into bore 113 the lower leading edge of the core body 121 cams against the inner surface of the stabilizer arms 114 thereby moving the stabilizer arms 114 radially outward through the corresponding slots 115 against a resilient biasing force from a first position to a second fully extended position. At the final position of the camming core 120, when the core body 121 has been fully inserted into bore 113 and the stabilizer arm(s) 114 are deployed into their fully extended position, the locking detents 116 of the stabilizer arms engage the locking circumferential recess 124 of the core body 121 to prevent the camming core 120 from disengaging the shell body 111. Moreover, the core body 121 provides a reinforcement to prevent the walls of the shell body 111 from bending or collapsing inward.

In one embodiment the implant 100 is configured and dimensioned such that when fully deployed the bone gripping protuberances 117 increase the frictional contact with the inner wall of the hole drilled in the bone into which the implant 100 is seated. However, bone tissue has some resiliency and can be deformed (without cracking or breaking) with sufficient pressure. In another embodiment the bone gripping protuberances 117 can be sized, and the implant 100 can be constructed, so that when fully deployed the bone gripping protuberances 117 press into the bone tissue and change the shape of the hole in the bone.

Referring to FIG. 4, to implant a prosthesis (not shown) a hole 11 is first drilled into a mass of bone tissue 10 by conventional methods. The size of the hole 11 is selected so as to be receptive to an implant 100 without an overly large diameter, which would cause the implant to move within the hole, or too small a diameter, which would render it extremely difficult or impossible to insert the implant. Rather, the diameter of the hole 11 must be just wide enough for the outer threaded surface 112 of the shell body 111 to bite into the inner wall of the hole so that the shell body 111 can be screwed into the hole. Next, the camming core 120 is screwed into the threaded bore 113 of the shell body 111 which deploys the stabilizer arms 114 outward, thereby fixing the implant securely in the bone.

Figures 5, 6:
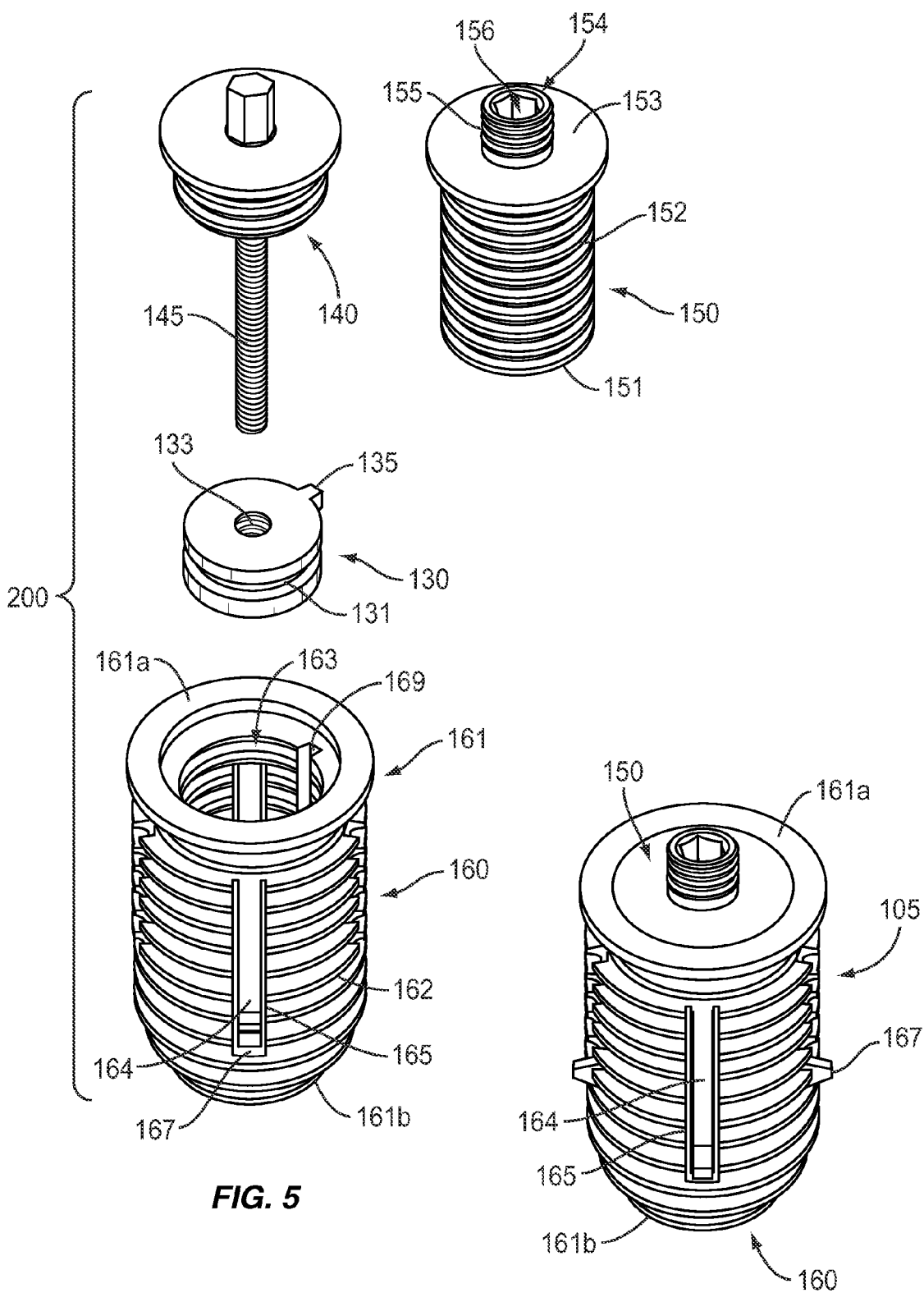
FIG. 5 is an exploded perspective view of an additional embodiment of the invention with an applicator.
FIG. 6 is a perspective view of the additional embodiment of the invention.

Referring now to FIGS. 5 and 6 an implant system 200 is illustrated which includes an implant 105 and applicator 140. Implant 105 includes a shell 160, a sled 130 which serves as a camming member, and a reinforcement core 150.

Shell 160 is similar to shell 110 except that it further includes a longitudinal guide slot 169 to prevent the sled 130 from rotating, as described below. More particularly, shell 160 includes a generally cylindrical body 161 with an upper end 161a and a lower end 161b. Shell body 161 further includes a threaded outer surface 162 and an inner threaded surface defining a threaded bore 163.

Shell body 161 further includes at least one, and preferably two or more, stabilizer arms 164, each associated with a corresponding longitudinal slot 165. Each stabilize arm 164 is flexibly attached to the shell body 161 at an upper bend point 164a and includes a depending elongated shaft 164b at the lower end of which is radially outward projecting bone gripping protuberance 167 and a radially inward projecting locking detent 166.

Figure 7A:
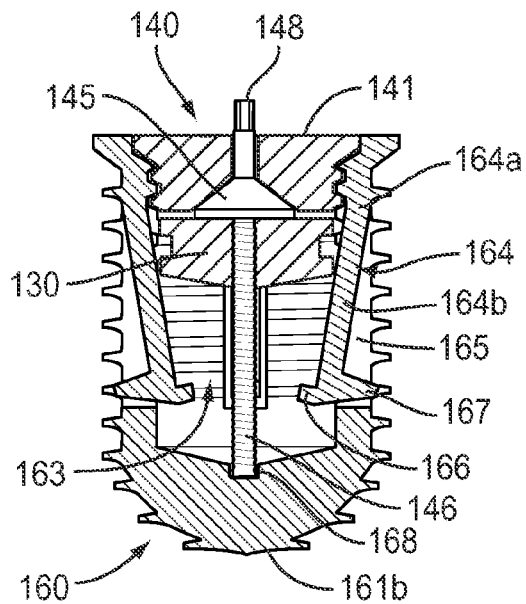
FIGS. 7A to 7E are a sequence of sectional views illustrating the deployment of the additional embodiment of the invention.
Figure 7B:
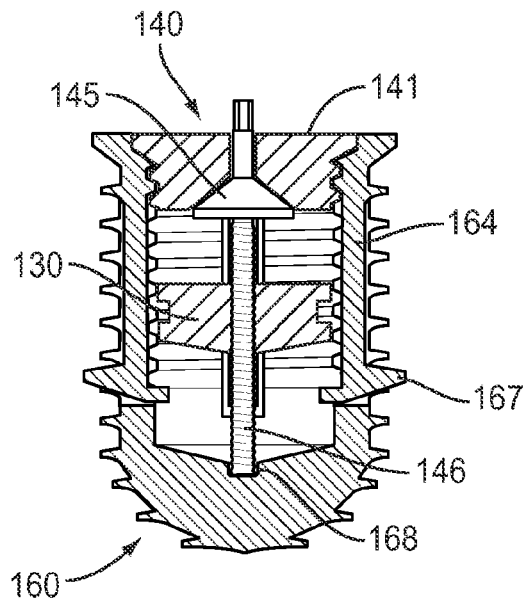
Figure 7C:
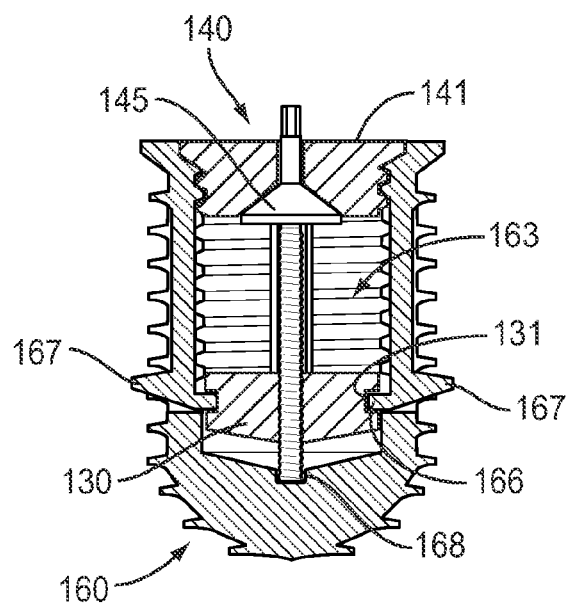

The stabilizer arms 164 can be integrally fabricated with shell body 161 as a single piece construction. Stabilizer arms 164 are resiliently biased to a radially inward first position as shown in FIG. 7A, but are flexibly movable against the biasing force to a second fully extended position as shown in FIG. 7C. In the first position of the stabilizer arm the bone gripping protuberance 167 is located within the bore 163. In the second fully extended position of the stabilizer arm 165, the bone gripping protuberance 167 is positioned beyond the outer surface 162 of the shell body 161 so as to grip the bone into which the implant 105 is secured. The stabilizer arm 164 is configured and dimensioned so as to be disposed through the corresponding slot 165.

The shell body 161 and stabilizer arms 164 can be fabricated from any medical grade material suitable for the purposes described herein. Such materials have been described herein.

Shell body 161 further includes a longitudinal guide slot 169 disposed on the inside surface of bore 163. Guide slot 169 is adapted to receive a corresponding key 135 in sled 130 as discussed below.

Sled 130 includes a generally cylindrical body having a circumferential locking recess 131 extending around the periphery thereof, and has a diameter dimensioned so as to slidably moved in a longitudinal direction through bore 163 of the shell body 161. An axial threaded bore 133 extends through the sled 130 and is adapted to receive the threaded shaft 145 of the applicator 140 as described below. Key 135 extends laterally from the periphery of the sled 130 and is adapted to slidably engage guide slot 169 of the shell body 161 so as to prevent rotation of the sled 130 within bore 163.

Referring now to FIGS. 5, 6, and 7A to 7E, applicator 140 includes a support frame 141 and a rotary transmission 145. Support frame 141 is a generally cylindrical piece having a threaded periphery 142 adapted to screw into the top portion of bore 163 of the shell body 161. Top surface 144 of the support frame 141 is slightly wider than the bore 163 so as to limit the insertion distance of the support frame 141 to the top portion of the bore 163. Support frame 141 further includes a central aperture 143 having an upper cylindrical portion 143*a* and a lower conical portion 143*b*.

The rotary transmission 145 includes a threaded drive shaft 146 fixed to a conical stabilizer 147 and a head 148 adapted to engage a tool for rotating the transmission 145. For example, head 148 can be a hex head adapted to be engaged by a wrench or other suitable tool. Referring in particular to FIGS. 7A to 7C, the threaded drive shaft 146 is adapted to be disposed through threaded bore 133 of the sled. The head 148 is adapted to extend through central aperture 143 so as to be accessible by a tool when the transmission is engaged with the support frame. The conical stabilizer is adapted to rotatably engage lower conical portion 143*b* of the support frame 141. The bottom end of the threaded drive shaft 146 is adapted to be rotatably received in a recess 168 at the bottom of bore 163, which stabilizes the drive shaft 146 against bending or twisting when it is rotated.

The reinforcement core 150 includes a generally cylindrical body 151 having a threaded circumferential surface 152 adapted to threadedly engage the bore 163 of the shell body 161. Top surface 153 has a diameter larger than that of bore 163 so as to limit the insertion of the reinforcement core 150 into the bore 163. When core 150 is fully inserted, the surface 153 is flush with upper end 161*a* of the shell body 161. The reinforcement core 150 also includes an axial projection 154 having a threaded our surface 155 and a central recess 156 configured so as to receive a turning tool, such as, for example, a hex wrench, which can be used to screw the reinforcement core 150 into the shell 160.

Figure 7D:
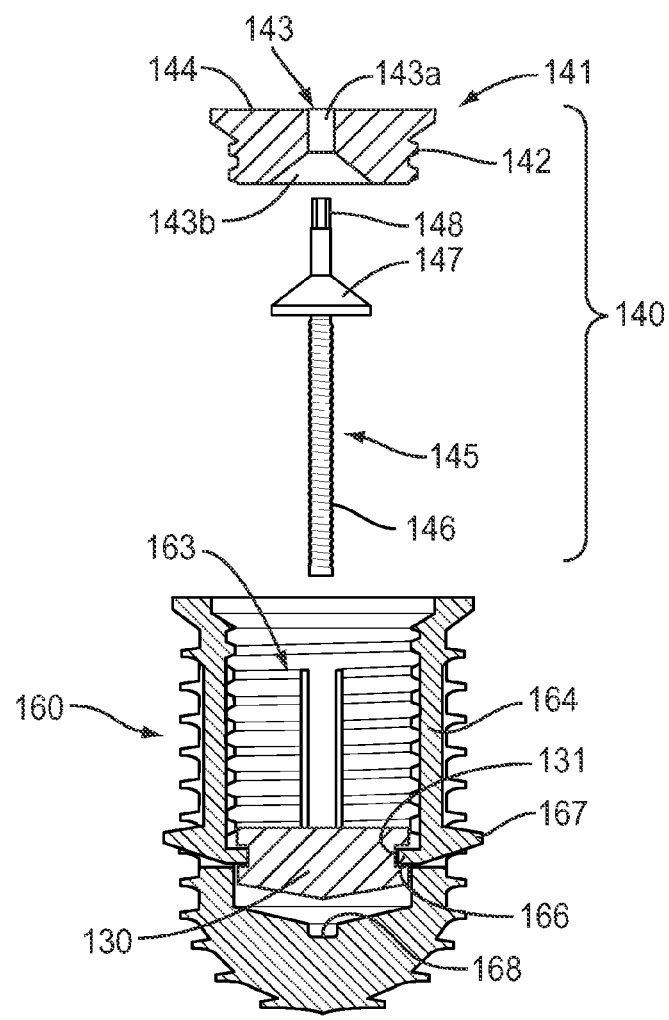
Figure 7E:
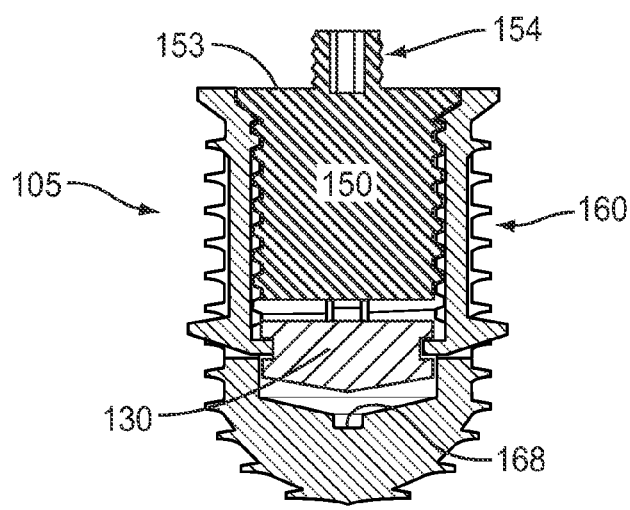

The implant system 200 is used as follows. First, a hole of suitable size is drilled into a bone mass. The implant is assembled with shell 160, sled 130 and applicator 140 as shown in FIG. 7A, and screwed into the hole for a snug fit. A tool is used to grip the head 148 of the transmission 145 and turn the drive shaft 146. As the sled 130 is prevented from rotating by the engagement of the key 135 in guide slot 169, it is forced to move vertically downward. Referring now to FIG. 7B, the downward movement of the sled 130 forces the sled 130 to cam against the inside surface of the stabilizer arms 164, thereby forcing them outward so that the bone gripping protuberances 167 press into the surrounding bone tissue. Referring now to FIG. 7C, when the sled has reached its full insertion into bore 163, the locking detents 166 of the stabilizer arms 164 resiliently engage the circumferential locking recess 131 of the sled, thereby securing the sled in the final position and preventing the sled from moving upward and out of the bore 163. Referring to FIG. 7D, the threaded drive shaft 146 is then turned in the opposite direction to unscrew it from the sled 130. The entire applicator 140 is then removed from the implant or may be removed in the process of disconnecting the shaft 146 from the sled 130. Referring to FIG. 7E, the reinforcement core 150 is then inserted into the bore 163. An adhesive, such as a cement, may be coated onto the exterior surface 152 to adhesively secure the reinforcement core 150 in the shell 160. Finally, a device, such as an abutment and/or prosthesis, may be attached to the top surface 153 of the reinforcement core 150 by threaded attachment to axial projection 154 and/or adhesive attachment by the use of a suitable adhesive.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. An implant comprising:
   a) a body having an upper end, a lower end, a longitudinal bore defined by a threaded interior surface, and an exterior surface including a thread projecting a first distance from the exterior surface;
   b) at least one stabilizer arm associated with a corresponding longitudinal slot in the body, said stabilizer arm being hingedly attached to the body and having a bone gripping protuberance projecting laterally outward therefrom, said stabilizer arm being movable from a first position, wherein said bone gripping protuberance is positioned within said longitudinal bore, and a second fully extended position, wherein said bone gripping protuberance extends beyond the exterior surface a second distance which is greater than the first distance, said stabilizer arm being resiliently biased to the first position;
   c) a camming member longitudinally movable through the longitudinal bore of said body from an initial position to a final position wherein the camming member includes a threaded exterior surface adapted to engage the threaded interior surface of the body, and means for mounting a device including an axial recess defined by a threaded interior surface or an upwardly projecting mounting member; and
   d) the stabilizer arm, wherein the arm includes a radially inward extending detent at the lower end portion thereof and the camming member includes a circumferential notch engageable with the detent when the camming member is moved to the final position, the detent and notch being configured to lock the camming member in the final position and lock the stabilizer arm in the fully extended second position.

2. The implant of claim 1, wherein the at least one stabilizer arm comprises more than one stabilizer arm.

3. The implant of claim 1 wherein the at least one stabilizer arm is integrally constructed with the body.

4. The implant of claim 1 wherein the stabilizer arm comprises an elongated longitudinally extending member with the bone gripping protuberance projecting from a lower end portion of the stabilizer arm.

5. The implant of claim 1 wherein said body is fabricated from a polymeric material or a metal.

6. The implant of claim 1 wherein the camming member comprises an upper rim having a diameter greater than the diameter of the bore of the body.

7. The implant of claim 1 wherein an exterior surface of the stabilizer arm is free of threads.

8. A method for delivering an implant comprising:
   a) drilling a hole into a bone;
   b) providing the implant of claim 1;
   c) inserting the implant into the hole in the bone; and
   d) moving the camming member from the initial position to the final position to secure the implant in the bone.

9. The method of claim 8 further including step (e) of inserting a reinforcing core into the bore of the implant body after the camming member is moved to its final position.

10. The method of claim 9 further including steps of
   f) confirming implant contact with the surrounding bone after insertion into the bone; and
   g) subsequently attaching a device.

* * * * *